US007241885B2

United States Patent
Kumar et al.

(10) Patent No.: US 7,241,885 B2
(45) Date of Patent: Jul. 10, 2007

(54) PROCESS FOR THE ISOLATION OF CRYSTALLINE IMIPENEM

(75) Inventors: Yatendra Kumar, Haryana (IN); Neera Tewari, Haryana (IN); Ram Chander Aryan, Delhi (IN); Bishwa Prakash Rai, Uttar Pradesh (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 45 days.

(21) Appl. No.: 10/478,624

(22) PCT Filed: May 20, 2002

(86) PCT No.: PCT/IB02/01718

§ 371 (c)(1),
(2), (4) Date: Jun. 17, 2004

(87) PCT Pub. No.: WO02/094773

PCT Pub. Date: Nov. 28, 2002

(65) Prior Publication Data

US 2004/0242865 A1    Dec. 2, 2004

(30) Foreign Application Priority Data

May 18, 2001    (IN) .................................. 595/01

(51) Int. Cl.
*C07D 477/20* (2006.01)
(52) U.S. Cl. ..................................................... 540/350
(58) Field of Classification Search ................. 540/350

See application file for complete search history.

(56) References Cited

U.S. PATENT DOCUMENTS

| 4,081,455 A * | 3/1978 | Kuhla .......................... 540/304 |
| 4,138,433 A * | 2/1979 | Kleiner et al. ............... 562/876 |
| 4,194,047 A | 3/1980 | Christensen et al. ......... 546/272 |
| 4,260,543 A | 4/1981 | Miller .................. 260/245.2 T |
| 4,292,436 A | 9/1981 | Liu et al. ..................... 560/148 |
| 4,374,772 A | 2/1983 | Hazen et al. .......... 260/245.2 T |
| 4,894,450 A | 1/1990 | Grabowski et al. .......... 540/350 |
| 5,245,069 A | 9/1993 | McManus .................... 558/148 |
| 2005/0004359 A1* | 1/2005 | Rai et al. ..................... 540/350 |

FOREIGN PATENT DOCUMENTS

WO    WO 02/36594    5/2002

OTHER PUBLICATIONS

Turner, "The Design of Organic Synthesis" (Elsevier, 1976), pp. 10 and 149.*
Chen et al., Angewandte Chemie Int. Ed. vol. 37, Issue 1/2, pp. 91-93 (1998).*
Crocker et al., "Comparison of the Crystallinity of Imipenem Samples by X-ray Diffraction of Amorphous Material", *Journal Of Pharmaceutical Sciences* 84(2):226-227 (1995).
Connolly et al., "Freeze Crystallization of Imipenem", *Journal of Pharmaceutical Sciences*, 85(2):174-177 (1996).

* cited by examiner

*Primary Examiner*—Mark L. Berch
(74) *Attorney, Agent, or Firm*—Jayadeep R. Deshmukh, Esq.; William D. Hare, Esq.

(57) ABSTRACT

The present invention relates to a cost effective and industrially advantageous process for the preparation of imipenem of high purity comprising the steps of treating an aqueous solution containing imipenem with an organic solvent, wherein the imipenem is not lyophilized; and isolating the pure crystalline imipenem monohydrate from the reaction mixture thereof.

8 Claims, No Drawings

PROCESS FOR THE ISOLATION OF CRYSTALLINE IMIPENEM

FIELD OF THE INVENTION

The present invention relates to a cost effective and industrially advantageous process for the preparation of imipenem of high purity.

BACKGROUND OF THE INVENTION

Imipenem monohydrate is the N-formimidoyl derivative of thienamycin, and has the structural Formula I.

FORMULA I

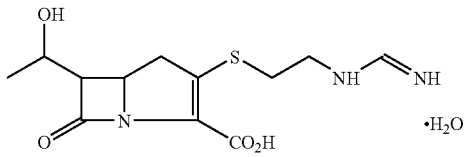

It is the first clinically available member of a new class of β-lactam antibiotics that possess the carbapenem ring system. Imipenem exhibits an extremely broad spectrum of activity against gram-positive and gram-negative aerobic and anaerobic species, which is partly due to its high stability in the presence of β-lactamases.

Imipenem was first disclosed in U.S. Pat. No. 4,194,047 and was obtained by lyophilization technique. The product obtained by lyophilization is found to be largely amorphous and stated to be thermodynamically unstable. The process also involves an initial purification through column chromatography using hydrophobic resins.

A thermodynamically stable crystalline monohydrate form of imipenem is disclosed in U.S. Pat. No. 4,260,543 which is obtained by crystallization of a lyophilized sample of imipenem. However, this process is not satisfactory on a commercial scale as it requires isolation of the product by column chromatography, lyophilization, followed by crystallization. Moreover, the prolonged process for isolation of the final product leads to degradation of imipenem, thus affecting the purity of the product.

U.S. Pat. No. 4,292,436 discloses crystalline imipenem by purifying the crude product by column chromatography. Further, Crocker et al. have reported in *J. Pharm. Sci.* 84, 226 (1995) that changes in lyophilization parameters result in varying degrees of crystallinity in the isolated imipenem samples. A variant method for preparing imipenem having a high degree of crystallinity by freeze crystallization process has been reported by Connolly et. al. in *J. Pharm. Sci,* 85, 174(1996). However, these processes are tedious, cumbersome and unsuitable for industrial use.

SUMMARY OF THE INVENTION

It is an object of the present invention to provide a simple, practical and efficient method for the preparation of crystalline imipenem monohydrate which is thermally stable, has a uniform degree of crystallinity and high purity.

The present invention relates to a process for the isolation of pure crystalline imipenem monohydrate from a solution containing imipenem. The process does not use capital intensive techniques of lyophilization or freeze crystallization as well as the time consuming purification process of column chromatography using expensive hydrophobic resins. The present invention thus fulfills the need for a process which is convenient to operate on a commercial scale.

Accordingly, the present invention provides a process for the isolation of pure crystalline imipenem monohydrate of Formula I,

FORMULA I

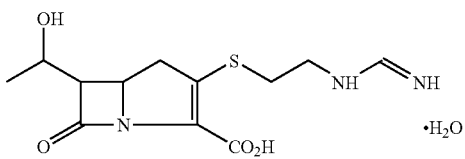

which comprises crystallizing imipenem monohydrate from a solution thereof which contains an organic, aqueous solvent or a mixture thereof, without using lyophilization, freeze drying or chromatographic techniques.

The solvent system from which the product may be crystallized will desirably be selected from organic solvents which are water-miscible organic solvents, either alone or in admixture with water.

Examples of such water-miscible organic solvents include lower alcohols such as methanol, ethanol, propanol and isopropanol; ketones such as acetone; glycol ethers such as monoethylene glycol; amides such as N,N-dimethylformamide, N,N-dimethylacetamide; lactams such as N-methylpyrrolidone and cyclic ethers such as tetrahydrofuran, dioxane, or mixture(s) thereof.

The crystallization step will desirably be carried out at low temperatures, for example at about 0° C. to about 15° C., and the concentration of imipenem in the solution from which crystallization will occur will generally be adjusted e.g. by evaporation of the solvent or by dilution so as to be neither too dilute nor too concentrated.

The crystallization may comprise the last stage or stages of a reaction in which the imipenem is formed. The reaction in which the imipenem is formed may be carried out by following any of the synthetic routes described in the prior art viz. U.S. Pat. Nos. 4,194,047; 4,292,436; 4,374,772; or 4,894,450 and are incorporated herein by reference, but will preferably be carried out in the manner described in the patent application filed concurrently herewith and exemplified as example 1 in this patent application.

Before carrying out the process of crystallization, the solution containing imipenem may be washed with an organic solvent having limited miscibility in water to remove organic impurities.

Also, pH of the solution of imipenem is adjusted, if required, to about 7 to 8 before washings to facilitate removal of impurities.

In the meaning of the present invention, the term "limited miscibility" shall also include water-immiscible solvents. Examples of such organic solvents include carboxylic acid esters such as ethyl acetate, higher alkyl ketones such as methylisobutyl ketone, chlorinated hydrocarbons such as dichloromethane, ethers such as diethyl ether, aromatic hydrocarbons such as toluene, and mixture(s) thereof.

DETAILED DESCRIPTION OF THE INVENTION

In the following section preferred embodiments are described by way of examples to illustrate the process of the invention. However, these are not intended in any way to limit the scope of the present invention.

PREPARATION OF IMIPENEM

Example 1

Step (a)—Preparation of enol phosphate intermediate p-Nitrobenzyl (3R, 5R, 6S)-2oxo-6-[(1 R)-1-hydroxyethyl)] carbapenem-3-carboxylate (30 g) was dissolved in a mixture of N,N-dimethylacetamide (300 ml) and dichloromethane (150 ml). The solution was cooled to −55° C. and dimethylaminopyridine (0.17 g) was added followed by diisopropylethylamine (26.7 g). The mixture was stirred for 5 minutes at about −55° C. and then a solution of diphenylchlorophosphate (25.4 g) in dichloromethane (30 ml) was added dropwise at −55 to −45° C. The reaction was stirred further for 30 minutes to obtain the enol phosphate ester.

Step (b)—Preparation of thienamycin ester

The reaction mixture from step (a) was further cooled to −70 to −75° C. and a solution of 2-aminoethanethiol hydrochloride (12 g) in N,N-dimethylacetamide (60 ml) was added in 10 minutes at −75 to −60° C. The reaction mixture was stirred for another 60 minutes to produce p-nitrobenzyl ester of thienamycin.

Step (c)—Preparation of p-nitrobenzyl ester of imipenem

To the above reaction mixture from step (b), was added diisopropylethylamine (16.0 g) and benzyl formimidate hydrochloride (20.0 g) at −50 to −55° C. The reaction was allowed to continue for about one and a half hour at the same temperature. The temperature was then raised to −20° C. and the reaction mixture was stirred for 20-30 minutes at this temperature to obtain a clear solution of imipenem ester.

Step (d)—Preparation of imipenem

The above clear solution obtained from step (c) was poured into a mixture of water (300 ml), isopropanol (150 ml) and N-methylmorpholine (26 g) maintained at 5-10° C. and the pH of the solution adjusted to 7.0 to 7.5. The solution was hydrogenated at 3-4 kg pressure for 2.5 hours at 10-25° C. over palladium-charcoal. The mixture was filtered and assayed for imipenem (80%, as determined by HPLC).

ISOLATION OF CRYSTALLINE IMIPENEM MONOHYDRATE

Example 2

The reaction mixture containing imipenem obtained at step (d) Example 1 was stirred with dichloromethane (900 ml) maintaining pH between 7.0 to 8.0 and the aqueous layer separated. The aqueous portion was degassed to remove dichloromethane and given activated carbon treatment. The filtered aqueous solution was mixed with isopropanol (400 ml) and stirred at 5-10° C. for 3 hours. The crystalline product so obtained was filtered, washed with isopropanol followed by acetone and dried at 35-40° C. for 1 hour to obtain crystalline imipenem monohydrate (9.0 g, purity 99% by HPLC).

Example 3

The process of Example 2 was repeated using acetone (400 ml) instead of isopropanol during crystallization. Crystalline imipenem monohydrate (8.0 g) was obtained in 99% purity (by HPLC).

Example 4

The aqueous portion obtained as in Example 2 was concentrated to 200 ml. The aqueous solution so obtained was given carbon treatment at 5-10° C. and the filtered solution was stirred with acetone (400 ml) at 5-10° C. for 3 hours to obtain crystalline imipenem monohydrate after filtration and drying (12.0 g, purity 98-99% by HPLC).

While the present invention has been described in terms of its specific embodiments, certain modifications and equivalents will be apparent to those skilled in the art and are intended to be included within the scope of the present invention.

What is claimed is:

1. A process for the preparation and isolation of pure crystalline imipenem monohydrate of Formula I, having a purity of 98% or more by HPLC, the process comprising:

FORMULA I $$\text{imipenem monohydrate structure} \cdot H_2O$$

(a) treating an aqueous solution containing imipenem with an organic solvent to get a mixture, wherein the imipenem is not lyophilized;
(b) stirring the mixture; and
(c) isolating the pure crystalline imipenem monohydrate from the mixture.

2. The process of claim 1 wherein the organic solvent comprises a water-miscible organic solvent.

3. The process of claim 2 wherein the water-miscible organic solvent is selected from the group consisting of methanol, ethanol, propanol, isopropanol, acetone, monoethylene glycol, N,N-dimethylformamide, N,N-dimethylacetamide, N-methylpyrrolidone, tetrahydrofuran, dioxane and mixture(s) thereof.

4. The process of claim 1 wherein the stirring is carried out at a temperature from about 0° C. to about 15° C.

5. The process of claim 1 wherein the solution containing imipenem is obtained directly from a reaction mixture.

6. The process of claim 1 wherein the solution containing imipenem is washed with a solvent comprising one or more of a carboxylic acid ester an alkyl ketone having six or more carbons, chlorinated hydrocarbon, ether, aromatic hydrocarbon, or a mixture thereof prior to treating with an organic solvent.

7. The process of claim 6 wherein the solvent is selected from the group consisting of ethyl acetate, methylisobutyl ketone, dichloromethane, diethyl ether, toluene and in mixture(s) thereof.

8. The process of claim 6 wherein the pH of the solution is adjusted to about 7 to 8 before carrying out the washing.

* * * * *